United States Patent
Ohi et al.

(10) Patent No.: US 9,788,803 B2
(45) Date of Patent: Oct. 17, 2017

(54) MEDICAL-DATA PROCESSING DEVICE AND RADIATION TOMOGRAPHY APPARATUS HAVING THE SAME

(75) Inventors: Junichi Ohi, Muko (JP); Yoshiyuki Yamakawa, Uji (JP); Ayako Akazawa, Kyotanabe (JP)

(73) Assignee: SHIMADZU CORPORATION, Kyoto-Shi, Kyoto (JP)

( * ) Notice: Subject to any disclaimer, the term of this patent is extended or adjusted under 35 U.S.C. 154(b) by 933 days.

(21) Appl. No.: 14/233,337

(22) PCT Filed: Sep. 15, 2011

(86) PCT No.: PCT/JP2011/005223
§ 371 (c)(1),
(2), (4) Date: Jan. 16, 2014

(87) PCT Pub. No.: WO2013/038452
PCT Pub. Date: Mar. 21, 2013

(65) Prior Publication Data
US 2014/0135622 A1    May 15, 2014

(51) Int. Cl.
*A61B 6/00*   (2006.01)
*A61B 6/02*   (2006.01)
*A61B 6/03*   (2006.01)

(52) U.S. Cl.
CPC .............. *A61B 6/027* (2013.01); *A61B 6/022* (2013.01); *A61B 6/037* (2013.01); *A61B 6/502* (2013.01); *A61B 6/5223* (2013.01)

(58) Field of Classification Search
CPC ......... A61B 6/022; A61B 6/027; A61B 6/037; A61B 6/502; A61B 6/5223
See application file for complete search history.

(56) References Cited

U.S. PATENT DOCUMENTS

2011/0096897 A1    4/2011   Tonami et al.

FOREIGN PATENT DOCUMENTS

| JP | 2005-106507 A | 4/2005 |
| WO | 2007/100955 A2 | 9/2007 |
| WO | 2009/066195 A1 | 5/2009 |
| WO | 2009/153860 A1 | 12/2009 |

OTHER PUBLICATIONS

International Search Report issued in International Application No. PCT/JP2011/005223 dated Dec. 6, 2011.

*Primary Examiner* — Ruth S Smith
(74) *Attorney, Agent, or Firm* — McDermott Will & Emery LLP

(57) ABSTRACT

The disclosure has an object to provide a medical-data processing device that allows generation of an MIP image suitable for diagnosis. With the medical-data processing device of the disclosure, intensity of a body surface region in three-dimensional space data is adjusted. The body surface region corresponds to a body surface of a stereoscopic image of a subject. Since the intensity of the body surface region is adjusted to be decreased, the maximum intensity is selected from a portion except for the body surface region to generate the MIP image. This prevents the body surface of the subject from appearing upon generating the MIP image. Therefore, the MIP image is obtainable having excellent visibility to the inside of the subject.

7 Claims, 5 Drawing Sheets

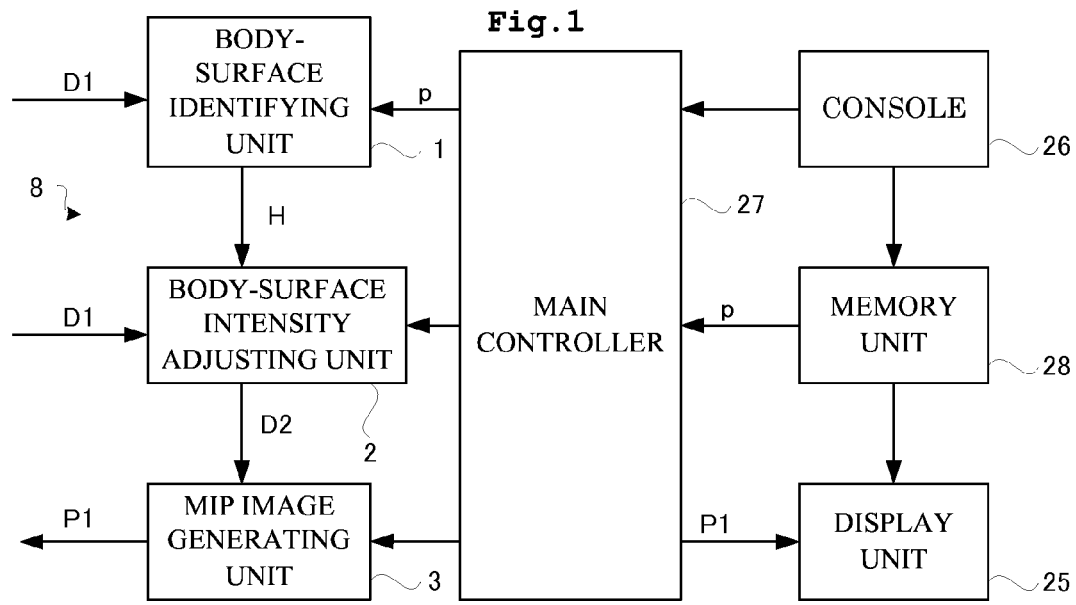
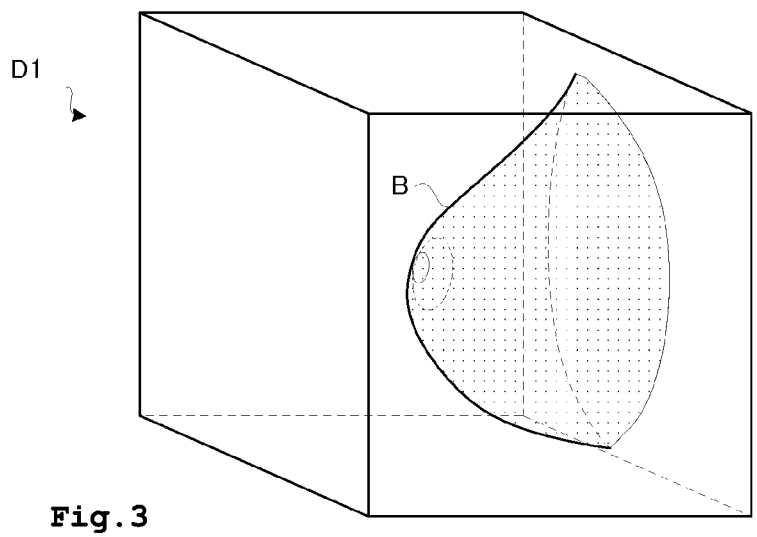
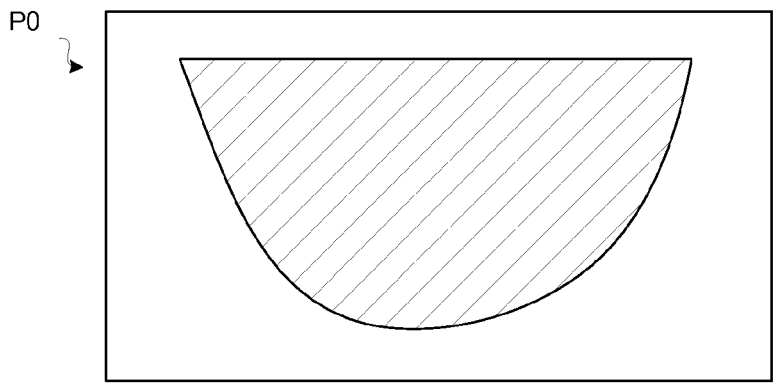

MEDICAL-DATA PROCESSING DEVICE AND RADIATION TOMOGRAPHY APPARATUS HAVING THE SAME

RELATED APPLICATIONS

This application is the U.S. National Phase under 35U.S.C. §371, of International Application No. PCT/JP2011/005223, filed on Sep. 15 2011, the disclosure of which Application is incorporated by reference herein.

TECHNICAL FIELD

The present invention relates to a medical-data processing device configured to generate an MIP (maximum-intensity projection) image and a radiation tomography apparatus having the medical-data processing device.

BACKGROUND ART

A medical institution is equipped with a radiation tomography apparatus for picking up tomographic images of a subject with radiation. Examples of such a radiation tomography apparatus include a PET (Positron Emission Tomography) apparatus configured to image radiopharmaceutical distribution within a subject. See, for example, Japanese Patent Publication (Translation of PCT Application) No. 2009-528139A.

Data obtained with the PET apparatus is three-dimensional data representing distribution intensity of radiopharmaceutical three-dimensionally. MIP imaging is one method of representing the three-dimensional data simply and conveniently as a two-dimensional image.

Description will be given of generating an MIP image. Three-dimensional data obtained with the PET apparatus contains a stereoscopic image of a subject. Here, a plane F relative to the stereoscopic image is to be considered. Next, a line N is to be considered. The line N passes through the plane F vertically and passes through the stereoscopic image V. See FIG. 10. The plane F is drawn as a line in FIG. 10 since the plane F is orthogonal to the plane of FIG. 10.

Here, considered is one of voxels of the stereoscopic image V on the line N. The voxel is a constitutional unit of three-dimensional data and corresponds to a pixel of a two-dimensional image. The voxel on the line N having the highest intensity corresponds to the maximum intensity of the line N.

The MIP image is obtained by placing the maximum intensity of the line N on an intersection Q of the line N and the plane F. That is, the maximum intensity of a plurality of lines parallel to the line N passing through the plane F is selected and placed successively, whereby an MIP image is generated. The MIP image generated in this way is an image with a remarkable configuration in the stereoscopic image V projected on the plane F.

Diagnosis with the MIP image allows rough determination of a portion of the subject where radiopharmaceutical concentrates. When the subject has inside thereof a concentrated portion of the radiopharmaceutical, it is determined that voxels with high intensity are collected in a portion of the three-dimensional data corresponding to the concentrated portion. The MIP image is generated while such the high intensity of the voxels is collected. Accordingly, diagnosis with the MIP image allows simple and convenient determination of a portion with high intensity in the three-dimensional data.

SUMMARY OF INVENTION

Technical Problem

The conventional construction as above, however, has the following problem.

Specifically, with the conventional construction, a body surface of a subject is obstructive to generation of the MIP image. Such a problem may arise. Radiopharmaceutical used in the PET apparatus has a tendency of concentrating in skin (body surface) of the subject. As the radiopharmaceutical, such a chemical compound that concentrates in cancer tissues is selected. Accordingly, a portion where the radiopharmaceutical concentrates may be more likely cancer tissues. On the other hand, the radiopharmaceutical also concentrates in normal tissues, for example, of the body surface.

Consequently, the radiopharmaceutical concentrates also in the body surface of the subject image in the three-dimensional data obtained with the PET apparatus. Diagnosis with the PET apparatus has a purpose of determining presence of cancer tissues inside the body surface. Therefore, the radiopharmaceutical concentrating on the body surface of the subject is obstructive to diagnosis.

Description will be given in detail of influences of the body surface of the subject. Upon generating the MIP image from the three-dimensional data, the voxel corresponding to the body surface of the subject may sometimes be of the maximum intensity on the line N. In this case, the body surface of the subject as normal tissues is projected on the MIP image to mask distribution of the radiopharmaceutical within the subject. Radiopharmaceutical with far higher concentration than that on the body surface may concentrate inside the body surface. However, with the conventional method of generating the MIP image, no concentrated portion of radiopharmaceutical as above is projected in the MIP image. Taking into consideration that the concentrated portion of radiopharmaceutical may be cancer tissues, cancer tissues other than skin cancer and cancer reaching the skin may be overlooked with the conventional method.

The present invention has been made regarding the state of the art noted above, and its object is to provide a medical-data processing device and a radiation tomography apparatus having the medical-data processing device that allows generation of an MIP image more suitable for diagnosis.

Solution to Problem

The present invention adopts the following construction for overcoming the above problem. One aspect of the present invention discloses a medical-data processing device for processing three-dimensional space data outputted from a tomographic apparatus. The medical-data processing device includes a body-surface intensity adjusting device configured to adjust intensity of a body surface region in the three-dimensional space data, the body surface region corresponding to a body surface of a stereoscopic image of a subject; and a maximum-intensity projection image generating device configured to generate a maximum-intensity projection image in accordance with the three-dimensional space data having the intensity adjusted. The body-surface intensity adjusting device decreases the intensity of the body surface region, whereby the maximum-intensity projection image generating device generates the image by selecting the maximum intensity from a portion of the three-dimensional space data except for the body surface region.

Operation and Effect

With the medical-data processing device according to the aspect of the present invention, the intensity of the body surface region in the three-dimensional space data is adjusted, the body surface region corresponding to the body surface of the stereoscopic image of the subject. The intensity of the body surface region is adjusted to be decreased. Consequently, the maximum intensity is selected from the portion except for the body surface region to generate the maximum-intensity projection image (MIP image). This avoids appearance of the body surface of the subject upon generating the MIP image. Accordingly, the MIP image is obtainable having excellent visibility to the inside of the subject.

Moreover, it is preferable that the medical-data processing device further includes a body-surface identifying device configured to identify the body surface region by performing contour extraction process to the three-dimensional space data, and that the body-surface intensity adjusting device operates relative to the body surface region identified by the body-surface identifying device.

Operation and Effect

The above construction is a detailed construction of the medical-data processing device according to the present invention. As noted above, the contour extraction process is performed to the three-dimensional space data to identify the body surface region. This achieves accurate determination of the body surface region. Consequently, the construction ensured to generate the MIP image with excellent visibility.

Moreover, it is more preferable that the body-surface identifying device of the medical-data processing device detects a boundary of the stereoscopic image of the subject and a void where no subject appears in the three-dimensional space data in accordance with whether or not the intensity of each voxel constituting the three-dimensional space data exceeds a threshold.

Operation and Effect

The above construction is a detailed construction of the medical-data processing device according to the present invention. As noted above, the body surface region is identified with use of the threshold, resulting in accurate determination of the body surface region. Consequently, such the construction ensures to generate the MIP image with excellent visibility.

The present invention also has disclosure relating to a radiation tomography apparatus having a function of the medical-data processing device. That is, another aspect of the present invention discloses a radiation tomography apparatus. The radiation tomography apparatus includes a detector ring configured to detect radiation emitted from a subject; a space data generating device configured to generate three-dimensional space data containing a stereoscopic image of the subject in accordance with output from the detector ring; a body-surface intensity adjusting device configured to adjust intensity of a body surface region in the three-dimensional space data, the region corresponding to a body surface of the stereoscopic image of the subject; and a maximum-intensity projection image generating device configured to generate a maximum-intensity projection image in accordance with the three-dimensional space data having the intensity adjusted. The body-surface intensity adjusting device decreases the intensity of the body surface region, whereby the maximum-intensity projection image generating device selects the maximum intensity from a portion other than the body surface region in the three-dimensional space data to generate the image.

Moreover, it is preferable that the radiation tomography apparatus includes a body-surface identifying device configured to identify the body surface region by performing contour extraction process to the three-dimensional space data, and that the body-surface intensity adjusting device operates relative to the body surface region identified by the body-surface identifying device.

Moreover, it is more preferable that the body-surface identifying device of the radiation tomography apparatus detects a boundary of the stereoscopic image of the subject and a void where no subject appears in the three-dimensional space data in accordance with whether or not the intensity of each voxel constituting the three-dimensional space data exceeds a threshold.

Operation and Effect

The above construction allows provision of the radiation tomography apparatus capable of obtaining the maximum-intensity projection image representing accurately the inside of the subject with no body surface of the subject appearing upon generating the MIP image.

Moreover, it is preferable that the radiation tomography apparatus is for breast inspection.

Operation and Effect

The above construction is a detailed construction of the radiation tomography apparatus according to the present invention. Typically, it is difficult to image breast cancer with radiopharmaceutical. However, the present invention allows accurate breast inspection since the MIP image faithfully representing the inside of the subject is obtainable.

Advantageous Effects of Invention

In the medical-data processing device of the present invention, the intensity in the body surface region in the three-dimensional space data is adjusted, the region corresponding to the body surface of the stereoscopic image of the subject. Since the intensity in the body surface region is adjusted to be decreased, and thus the image is generated by selecting the maximum intensity from the portion except for the body surface region upon generating the MIP image. This prevents the body surface of the subject from appearing upon generating the MIP image. Consequently, the MIP image is obtainable having excellent visibility to the inside of the subject.

BRIEF DESCRIPTION OF DRAWINGS

FIG. 1 is a function block diagram of a medical-data processing device according to one embodiment.

FIG. 2 is a schematic view illustrating space data according to the embodiment.

FIGS. 3 to 6 are schematic views each illustrating a body-surface identifying unit according to the embodiment.

DESCRIPTION OF EMBODIMENTS

Figure 4:
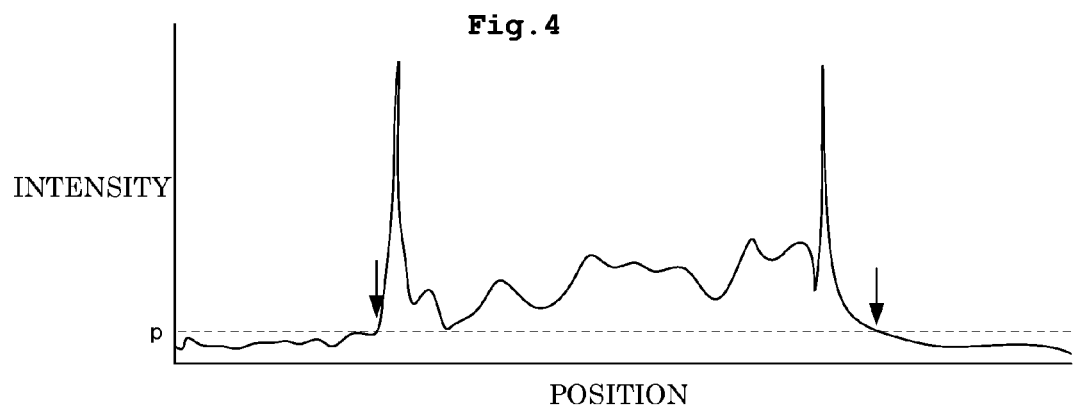

Description will be given hereinafter of embodiments with reference to drawings.

Embodiment 1
<Whole Construction of Medical-Data Processing Device>

A medical-data processing device (hereinafter, simply referred to as a data processor 8) according to Embodiment 1 outputs an MIP image P1 upon receiving three-dimensional space data (hereinafter, simply referred to as space data D1) containing a stereoscopic image of a subject, as illustrated in FIG. 1. The space data D1 is obtained by reconstructing raw data on a three-dimensional space with various tomographic images, the raw data being obtained upon radiography of a stereoscopic image of a subject. Examples of raw data include sinogram or list data. The MIP image P1 corresponds to the maximum-intensity projection image in the present invention. The space data D1 corresponds to the three-dimensional space data in the present invention.

In the space data D1, distribution of radiopharmaceutical within the subject is expressed by intensity. A void in the space data D1 where no subject image appears has an intensity value lower than that of a subject image. In addition, much radiopharmaceutical concentrates in the skin of the subject image. This is because the radiopharmaceutical has a tendency of concentrating not only in cancer tissues but also in normal skin.

As illustrated in FIG. 1, the data processor 8 of Embodiment 1 includes a body-surface identifying unit 1. The body-surface identifying unit 1 identifies a portion in the space data D1 by performing contour extraction process to the space data D1. The portion (a portion containing a body surface: a body surface region R) corresponds to a body surface of the stereoscopic image of the subject. In addition, the data processor 8 includes a body-surface intensity adjusting unit 2 and an MIP image generating unit 3. The body-surface intensity adjusting unit 2 adjusts the intensity of the body surface region R in the space data D1. The MIP image generating unit 3 generates an MIP image P1 in accordance with the space data D1 having the adjusted intensity. The body-surface identifying unit 1 corresponds to the body-surface identifying device in the present invention. The body-surface intensity adjusting unit 2 corresponds to the body-surface intensity adjusting device in the present invention. The MIP image generating unit 3 corresponds to the maximum-intensity projection image generating device in the present invention.

As illustrated in FIG. 2, the space data D1 is three-dimensional matrix data containing the stereoscopic image of the subject in the three-dimensional space. The space data D1 has voxels in each of which data (e.g., intensity) detected by the radiation tomography apparatus is arranged. The space data D1 is obtained while the subject is guided to a field of view of the radiation tomography apparatus. The voxels are arranged within a space of a rectangular solid to constitute the space data D1. The space data D1 is defined as a rectangular solid since this shape is advantageous for holding the data. The space data D1 of the rectangular solid contains inside thereof the entire field of view of the radiation tomography apparatus in a cylindrical shape. Here, the space data D1 is illustrated as one example having an image of a breast B obtained with a PET apparatus for breast inspection. In FIG. 2, a hatched breast B represents skin of the breast B. The skin corresponds to the body surface in the present invention.

As above, the space data D1 corresponds to the three-dimensional reconstruction data prior to generation of the tomographic image with the radiation tomography apparatus.

Description will be given of operations of the body-surface identifying unit 1. The body-surface identifying unit 1 firstly generates a tomographic image P0 obtained by slicing the space data D1 along a virtual plane. Thus, a plurality of tomographic images P0 is to be generated for a plurality of virtual planes parallel to one another. The stereoscopic image of the subject is to be separated into a plurality of tomographic images P0. FIG. 3 illustrates one of the tomographic images P0 generated with the body-surface identifying unit 1.

Next, the body-surface identifying unit 1 generates a profile about a line crossing the tomographic image P0. The profile has a relationship between intensity and a position on the line. A plurality of profiles is generated for a plurality of lines parallel to one another. Thus, the tomographic image P0 is separated into a plurality of profiles. FIG. 4 illustrates one of the profiles generated with the body-surface identifying unit 1. Two peaks in FIG. 4 each represent a contact portion to the skin (body surface) of the subject. Since radiopharmaceutical has a property of concentrating on the body surface, a position in the profile corresponding to the body surface has a high intensity value.

The body-surface identifying unit 1 successively obtains intensity of one end to the other end of the profile to identify positions where the intensity exceeds a threshold p. Then, the body-surface identifying unit 1 performs similar operation from the other end to one end of the profile. FIG. 4 illustrates the positions identified by the body-surface identifying unit 1 by arrows. Here, one end and the other end of the profile each correspond to a void where no subject image appears. The void has an intensity value lower than that of the subject image, and is also called a background.

When the intensity value is seen from one end to the other end of the profile step by step, a position appears where the intensity becomes higher. Taking into consideration that the subject image has an intensity value higher than the void, the void is shifted to the subject image at this position. Thus, the body-surface identifying unit 1 detects a boundary of the stereoscopic image of the subject and the void where no subject appears in the space data D1 by determining whether or not the intensity of each voxel constituting the space data D1 exceeds the threshold.

Figure 5:
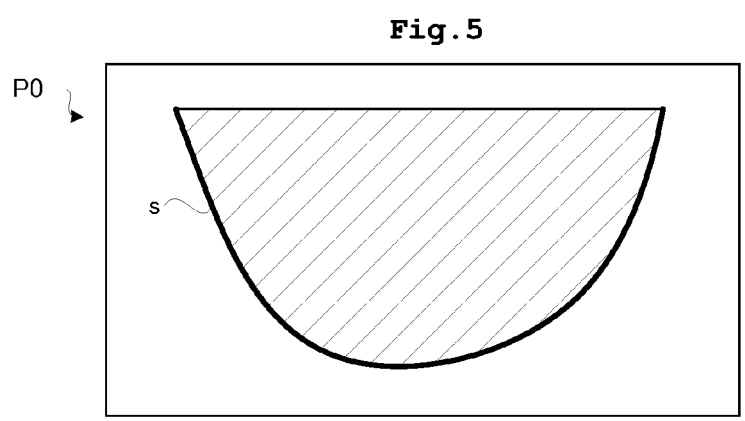

Here, numeral s in FIG. 5 denotes the boundary of the subject image and the void detected with the body-surface identifying unit 1. The boundary s is detected by identifying a position where the intensity exceeds the threshold p by the body-surface identifying unit 1 in accordance with a plurality of profiles.

Figure 6:
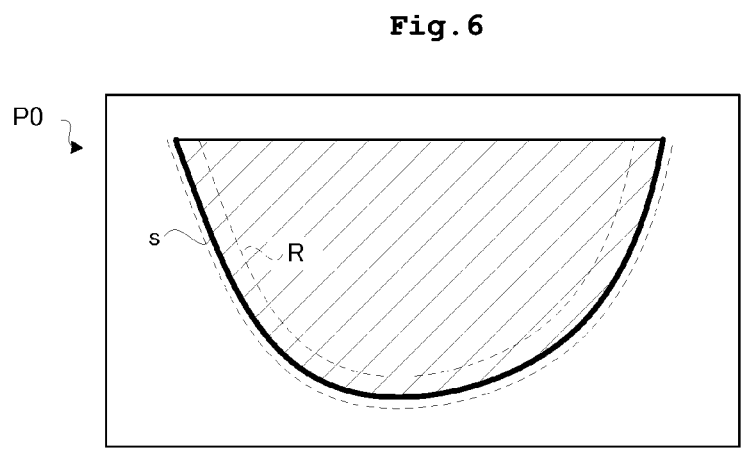

FIG. 6 illustrates identification of the body surface of the subject by the body-surface identifying unit 1 in accordance with the boundary s. The body-surface identifying unit 1 sets a body surface region R having a given width from the boundary toward the void. The body surface region R is also set so as to have a given width from the boundary s toward the subject image. The width of the body surface region R toward void is larger than that toward the subject image. Accordingly, a portion of the body surface is certainly removable. This ensures to remove a portion of the body surface of the subject with high intensity. In FIG. 6, a U-shaped area enclosed with dotted lines represents the body surface region identified by the body-surface identifying unit 1.

The position of the body surface region R identified by the body-surface identifying unit 1 is represented by position data H. The position data H is sent to the body-surface intensity adjusting unit 2. The body-surface intensity adjusting unit 2 recognizes a position of the body surface region R in the space data D1 in accordance with the position data H. Then, the body-surface intensity adjusting unit 2 makes an intensity value of the voxel within the body surface region R to 0. This causes elimination of the body surface in the space data D1 with high intensity of the stereoscopic image of the subject.

Figure 7:
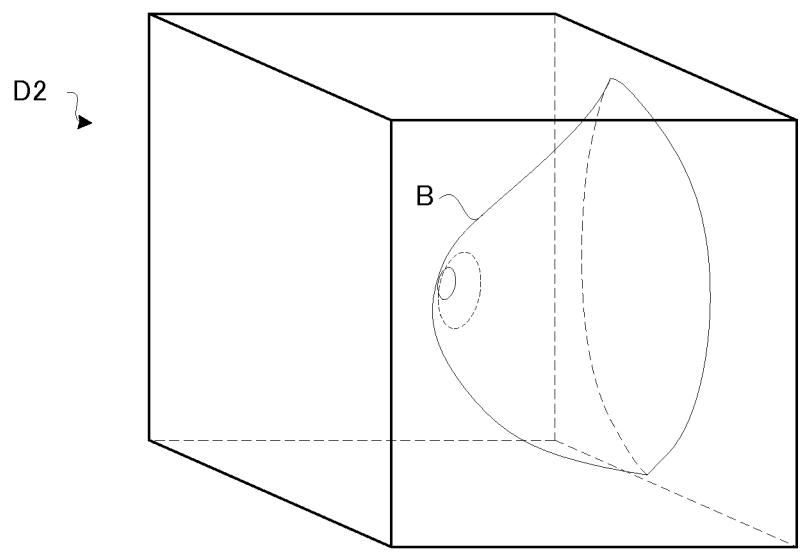
FIG. 7 is a schematic view illustrating space data having corrected intensity according to the embodiment.

FIG. 7 illustrates three-dimensional space data (intensity-corrected space data D2) generated by performing intensity correction made by the body-surface intensity adjusting unit 2 to the space data D1. The intensity-corrected space data D2 contains the subject image having the body surface removed therefrom. The subject image in FIG. 7 has no body surface of the subject (breast B) in FIG. 2, and thus the inside is exposed.

Figure 8:
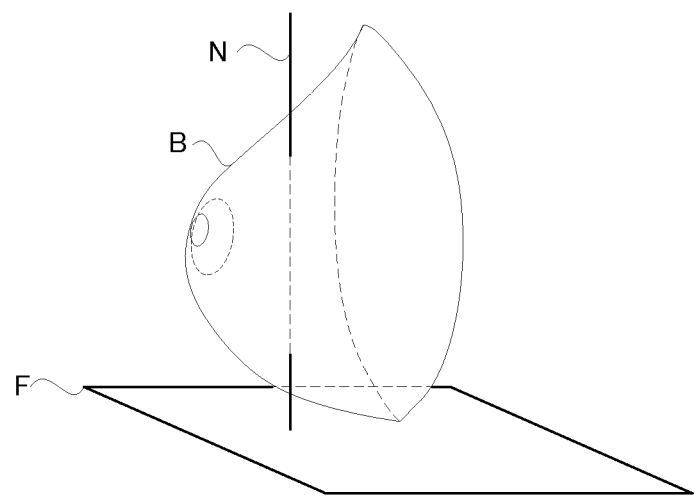
FIG. 8 is a schematic view illustrating an MIP image generating unit according to the embodiment.

The intensity-corrected space data D2 is sent to the MIP image generating unit 3 from the body-surface intensity adjusting unit 2, as shown in FIG. 1. The MIP image generating unit 3 generates an MIP image P1 in accordance with the intensity-corrected space data D2. The MIP image P1 is to be described. As illustrated in FIG. 8, the MIP (maximum-intensity projection) image is a two-dimensional image when the intensity-corrected space data D2 is projected on a plane F. The MIP image P1 is generated as under. Firstly, a plane F where the MIP image P1 is to be generated and a line N orthogonal to the plane F are assumed. Voxel data through which the line N passes represents intensity. Here, the maximum intensity is selected from the intensity, and is placed at a position in the plane F through which the line N passes. In other words, the maximum intensity is to be selected from any position on the dotted line in FIG. 8 where the line N crosses a three-dimensional image of the subject. This operation is performed to other positions in the plane F, achieving obtainment of the MIP image P1 having the maximum intensity in each line arranged two-dimensionally.

When the MIP image generating unit 3 generates the MIP image P1, no intensity value at the position on the body surface of the subject image appears in the MIP image. This is because the intensity on the body surface of the subject is substituted for 0 in the intensity-corrected space data D2, and thus the body surface of the subject is eliminated from the data. Consequently, the MIP image P1 is an image containing the inside from the body surface.

In other words, the body-surface intensity adjusting unit 2 decreases the intensity of the body surface region R, whereby the MIP image generating unit 3 generates the MIP image P1 by selecting the maximum intensity from the portion except for the body surface region R.

A main controller 27 is provided for performing control to each of controllers en bloc. The main controller 27 has a CPU, and provides each of the controllers 1, 2, and 3 by executing various programs. A console 26 is provided for inputting operator's commands. A memory unit 28 stores the threshold p used in the body-surface identifying unit 1. A display unit 25 is provided for displaying the generated MIP image P1.

As noted above, with the data processor 8 of the present invention, the intensity of the body surface region R in the space data D1 is adjusted, the region R corresponding to the body surface of the stereoscopic image of the subject. Since the intensity of the body surface region R is adjusted to be decreased, the maximum intensity is selected from the portion except for the body surface region R to generate the maximum-intensity projection image (MIP image P1). This prevents the body surface of the subject from appearing upon generating the MIP image P1. Consequently, the MIP image P1 is obtainable having excellent visibility to the inside of the subject.

Moreover, as noted above, the contour extraction process is performed to the space data D1 to identify the body surface region R, resulting in accurate determination of the body surface region R. Therefore, the construction as above ensures to generate the MIP image P1 having excellent visibility.

Furthermore, the body surface region R is identified as above with the threshold p, resulting in accurate determination of the body surface region R.

Embodiment 2

Next, an embodiment of a radiation tomography apparatus according to the present invention will be described hereinafter with reference to drawings. Gamma-rays in Embodiment 2 are one example of the radiation in the present invention. Embodiment 2 discloses a mammography device for breast inspection. Specifically, the radiation tomography apparatus of Embodiment 2 generates a tomographic image by imaging radiopharmaceutical distributed in the breast B.

<Whole Construction of Radiation Tomography Apparatus>

Figure 9:
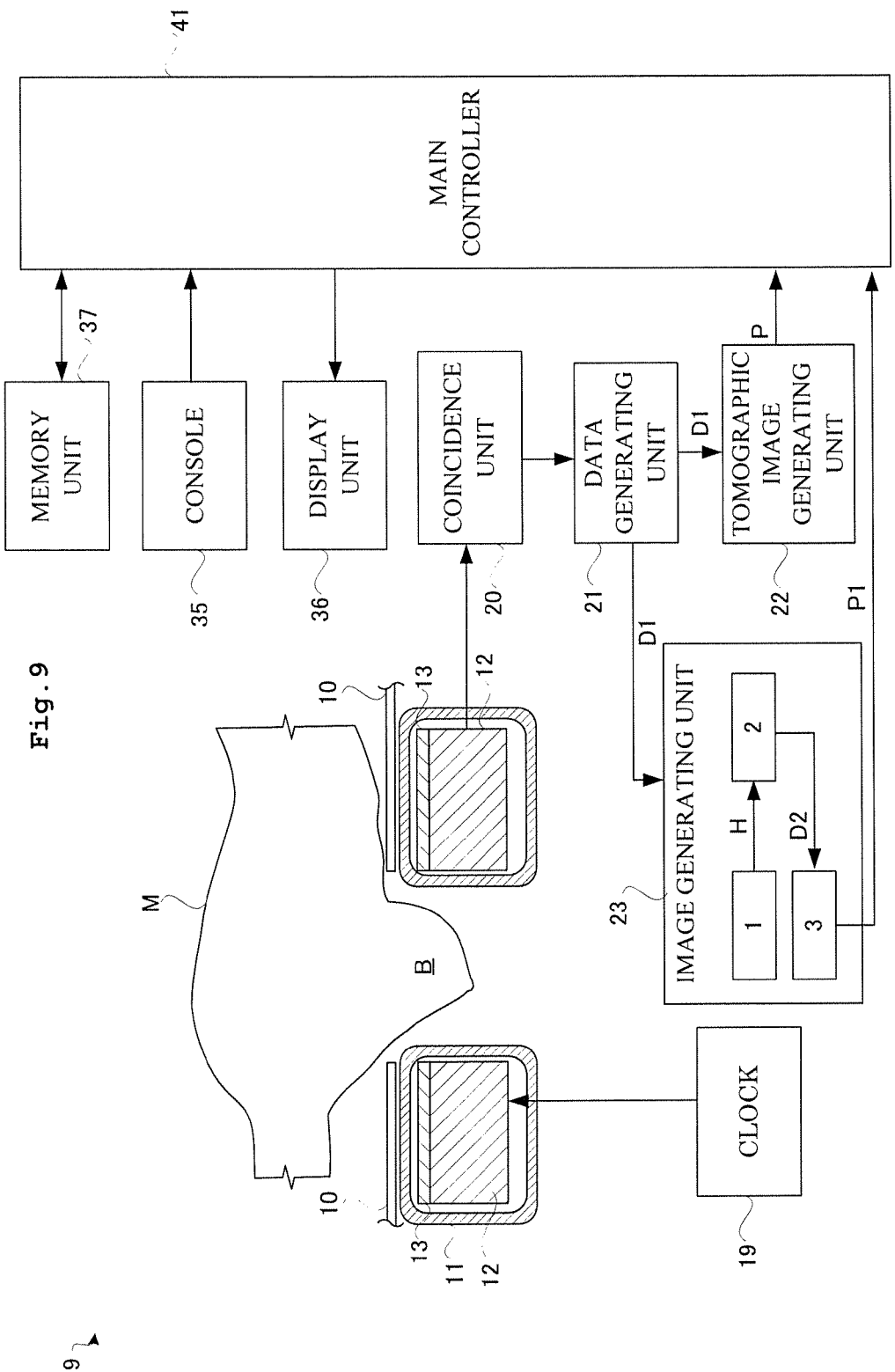
FIG. 9 is a function block diagram illustrating a radiation tomography apparatus according to another embodiment.
Figure 10:
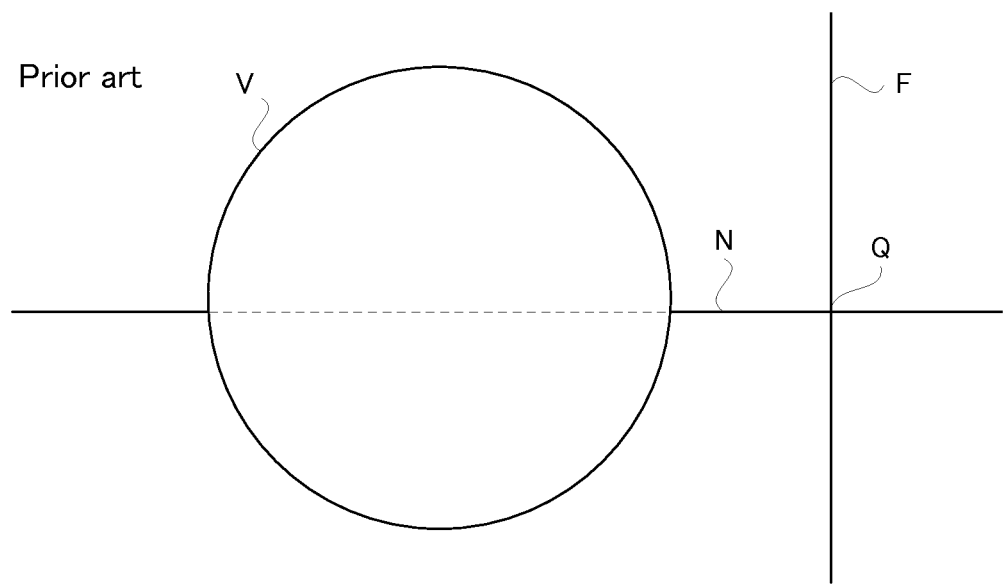
FIG. 10 is a schematic view of a conventional apparatus.

FIG. 9 is a functional block diagram illustrating a detailed configuration of a radiation tomography apparatus according to Embodiment 2. A radiation tomography apparatus 9 according to Embodiment 2 includes a gantry 11 with an opening configured to insert a breast B of a subject M in a z-direction; and a detector ring 12 in a ring shape provided inside the gantry 11 and configured to insert the breast B of the subject M. The opening in the detector ring 12 is cylindrical (strictly speaking, a regular octagonal prism) extending in the z-direction. Accordingly, the detector ring 12 itself extends in the z-direction. Here, the opening of the detector ring 12 corresponds to a field of view where the radiation tomography apparatus 9 allows generation of a tomographic image P. The z-direction is in a direction where the central axis of the detector ring 12 extends.

A top board 10 is provided for placing a subject M lying on her stomach. The top board 10 includes a hole passing thereinto in the z-direction for inserting the breast B of the subject M. Here, the breast B is inserted through the hole into the detector ring 12. The opening of the gantry 11 is directed upward vertically. Thus, the breast B is to be inserted into the opening vertically toward a lower side of the opening.

A shield plate 13 is composed of Tungsten or lead. See FIG. 9. Since radiopharmaceutical exists in a portion of the subject M other than the breast B, annihilation gamma-ray pairs are also generated from the portion. Incidence of such the annihilation gamma-ray pairs from the portion other than a site of interest into the detector ring 12 causes obstruction of picking up a tomographic image. Accordingly, the shield plate 13 in the ring shape is provided so as to cover one end of the detector ring 12 adjacent to the subject M in the z-direction.

A clock 19 sends time information with serial numbers to the detector ring 12. The time information about time of detecting gamma-rays is given to the detection signal outputted from the detector ring 12, and then the signal is inputted into a coincidence unit 20 to be mentioned later.

Description will be given of the detector ring 12. Eight radiation detectors are arranged in a virtual circle on a plane orthogonal to the z-direction (the central axis direction) to form a unit ring of the detector ring 12. Three unit rings are arranged in the z-direction to form the detector ring 12.

The detection signal outputted from the detector ring 12 is sent to the coincidence unit 20 (see FIG. 9). Two gamma-rays incident on the detector ring 12 simultaneously is an annihilation gamma-ray pair derived from the radiopharmaceutical within the subject. The coincidence unit 20 counts frequency of detecting the annihilation gamma-ray pair for every combination of two scintillation counter crystals constituting the detector ring 12, and the resultant is sent to a tomographic image generating unit 22. Here, time information that the clock 19 gives to the detection signal is used for determination of coincident property of the detection signal from the coincidence unit 20.

A data generating unit 21 generates space data D1 containing the stereoscopic image of the breast of the subject M in accordance with coincidence data outputted from the coincidence unit 20. The tomographic-image generating unit 22 generates a tomographic image P obtained when the opening of the detector ring 12 is cut along a plane. The data generating unit 21 corresponds to the space-data generating device in the present invention.

An image generating unit 23 expresses the body-surface identifying unit 1, the body-surface intensity adjusting unit 2, and the MIP image generating unit 3 in Embodiment 1 collectively.

A display unit 36 displays the tomographic image P and the MIP image P1 generated by the tomographic image generating unit 22 and the image generating unit 23, respectively. A memory unit 37 stores all parameters, such as the detection signal outputted from the detector ring 12, the coincidence data and the tomographic image P generated by the coincidence unit 20 and the image generating unit 23, respectively, and the threshold. The parameters are referred to upon operation of each unit.

Moreover, the radiation tomography apparatus 9 includes a main controller 41 configured to control each section en bloc. The main controller 41 has a CPU, and provides each of controllers 19, 20, 21, 22, and 23 by executing various programs. The above sections may each be divided into a controller that performs their functions.

<Operation of Radiation Tomography Apparatus>

Next, description will be given of operation of the radiation tomography apparatus. Upon inspecting the breast B with the radiation tomography apparatus 9 according to Embodiment 2, firstly the subject M with radiopharmaceutical administered thereto by injection in advance lies on his/her stomach on the top board 10 (subject placing step S1).

When adjusting a position of the subject M is completed, an operator issues a command via a console 35 to start picking up a tomographic image, whereby the detector ring 12 starts detection of an annihilation gamma-ray pair (radiography starting step S2). The tomographic-image generating unit 22 images the detected annihilation gamma-ray pairs to generate a tomographic image P. On the other hand, the image generating unit 23 images the detected annihilation gamma-ray pairs to generate an MIP image P1. The tomographic image P and the MIP image P1 are displayed on the display unit 36 to complete operation of the radiation tomography apparatus in Embodiment 2.

The construction as above allows provision of the radiation tomography apparatus capable of obtaining the MIP image P1 representing the inside of the subject M accurately with no body surface of the subject M appearing therein upon generating the MIP image P1.

Typically, it is difficult to image breast cancer with use of radiopharmaceutical. However, the present invention allows accurate breast inspection since the MIP image P1 faithfully representing the inside of the subject M is obtainable.

The present invention is not limited to the foregoing configuration, but may be modified as follows.

(1) The body-surface intensity adjusting unit 2 sets the intensity value of the body surface to 0. The present invention, however, is not limited to this. That is, the body-surface intensity adjusting unit 2 may substitute the intensity value of the body surface for a value other than 0. In this case, the intensity value may be substituted, for example, for a value lower than an average value of the intensity values within the subject. This achieves obtainment of intensity-corrected space data D2 with the structure of the body surface remaining therein.

(2) The body-surface identifying unit 1 identifies the body surface of the subject with the threshold p. The present invention, however, is not limited to this. That is, the body surface of the subject may be identified with use of a dynamic contour model such as Snakes and a level set method.

(3) The above construction is for breast inspection. The present invention, however, is not limited to this. That is, the present invention is applicable to various types of PET apparatus such as for inspection for a whole-body of a subject, inspection for a head of a subject, and inspection for smaller animals.

(4) The above construction is applied to the PET apparatus. The present invention, however, is not limited to this. The present invention is applicable to other types of tomography apparatus, such as a SPECT apparatus, an MIR apparatus, and a CT apparatus.

(5) In each of the foregoing embodiments, the scintillation counter crystal is composed of LYSO. Alternatively, the scintillation counter crystal may be composed of another materials, such as LGSO ($Lu_{2(1-x)}G_{2x}SiO_5$) and GSO ($Gd_2SiO_5$), in the present invention. This modification can provide a method of manufacturing a radiation detector of low price.

INDUSTRIAL APPLICABILITY

As described above, the present invention is suitable for an image processor for medical uses.

The invention claimed is:

1. A medical-data processing device for processing three-dimensional space data outputted from a tomographic apparatus, the medical-data processing device comprising:
    a body-surface identifying device configured to identify a body surface region by performing contour extraction process to the three-dimensional space data, the body surface region corresponding to a body surface of a stereoscopic image of a subject;
    an intensity adjusting device configured to adjust intensity of the body surface region in the three-dimensional space data; and
    an image generating device configured to generate a maximum-intensity projection image in accordance with the three-dimensional space data having the intensity adjusted, wherein
    the intensity adjusting device decreases the intensity of the body surface region, whereby the image generating device generates the image by selecting the maximum intensity from a portion of the three-dimensional space data except for the body surface region.

2. The medical-data processing device according to claim 1, wherein the intensity adjusting device operates relative to the body surface region identified by the body-surface identifying device.

3. The medical-data processing device according to claim 1, wherein the body-surface identifying device detects a boundary of the stereoscopic image of the subject and a void where no subject appears in the three-dimensional space data in accordance with whether or not the intensity of each voxel constituting the three-dimensional space data exceeds a threshold.

4. A radiation tomography apparatus, comprising:
a detector ring configured to detect radiation emitted from a subject;
a space data generating device configured to generate three-dimensional space data containing a stereoscopic image of the subject in accordance with output from the detector ring;
a body-surface identifying device configured to identify a body surface region by performing contour extraction process to the three-dimensional space data, the body surface region corresponding to a body surface of the stereoscopic image of the subject;
an intensity adjusting device configured to adjust intensity of the body surface region in the three-dimensional space data; and
an image generating device configured to generate a maximum-intensity projection image in accordance with the three-dimensional space data having the intensity adjusted, wherein
the intensity adjusting device decreases the intensity of the body surface region, whereby the image generating device selects the maximum intensity from a portion other than the body surface region in the three-dimensional space data to generate the image.

5. The radiation tomography apparatus according to claim 4, wherein the intensity adjusting device operates relative to the body surface region identified by the body-surface identifying device.

6. The radiation tomography apparatus according to claim 4, wherein the body-surface identifying device detects a boundary of the stereoscopic image of the subject and a void where no subject appears in the three-dimensional space data in accordance with whether or not the intensity of each voxel constituting the three-dimensional space data exceeds a threshold.

7. The radiation tomography apparatus according to claim 4, wherein the subject is a breast.

\* \* \* \* \*